United States Patent
Wen et al.

(10) Patent No.: US 7,502,498 B2
(45) Date of Patent: Mar. 10, 2009

(54) PATIENT MONITORING APPARATUS

(75) Inventors: Huafeng Wen, Redwood Shores, CA (US); Bao Tran, Santa Clara, CA (US)

(73) Assignee: Available For Licensing, San Jose, CA (US)

( * ) Notice: Subject to any disclaimer, the term of this patent is extended or adjusted under 35 U.S.C. 154(b) by 746 days.

(21) Appl. No.: 10/938,783

(22) Filed: Sep. 10, 2004

(65) Prior Publication Data

US 2006/0056655 A1    Mar. 16, 2006

(51) Int. Cl.
    *G06K 9/00*    (2006.01)
(52) U.S. Cl. ...................................... 382/128; 128/922
(58) Field of Classification Search ................ 382/100, 382/128, 181, 190, 195, 206; 128/922
    See application file for complete search history.

(56) References Cited

U.S. PATENT DOCUMENTS

| | | | |
|---|---|---|---|
| 4,234,926 A | 11/1980 | Wallace et al. |
| 4,275,742 A | 6/1981 | Faisandier |
| 4,320,767 A | 3/1982 | Villa-Real |
| 4,412,545 A | 11/1983 | Okino et al. |
| 4,420,000 A | 12/1983 | Bailey |
| 4,537,202 A | 8/1985 | Mancini et al. |
| 4,557,270 A | 12/1985 | John |
| 4,595,018 A | 6/1986 | Rantala |
| 4,656,319 A | 4/1987 | Bially |
| 4,679,144 A | 7/1987 | Cox et al. |
| 4,778,449 A | 10/1988 | Weber et al. |
| 4,807,642 A | 2/1989 | Brown |
| 4,819,648 A | 4/1989 | Ko |
| 4,862,359 A | 8/1989 | Trivedi et al. |
| 4,869,261 A | 9/1989 | Penaz |
| 4,880,013 A | 11/1989 | Chio |
| 4,907,597 A | 3/1990 | Chamoun |
| 4,922,229 A | 5/1990 | Guenst |
| 4,964,411 A | 10/1990 | Johnson et al. |
| 5,090,418 A | 2/1992 | Squires et al. |
| RE34,015 E | 8/1992 | Duffy |
| 5,140,990 A | 8/1992 | Jones et al. |
| 5,161,529 A | 11/1992 | Stotts et al. |
| 5,162,991 A | 11/1992 | Chio |
| 5,271,411 A | 12/1993 | Ripley et al. |
| 5,285,793 A | 2/1994 | Slovut et al. |
| 5,287,859 A | 2/1994 | John |
| 5,309,916 A | 5/1994 | Hatschek |
| 5,331,969 A | 7/1994 | Silberstein |
| 5,361,775 A | 11/1994 | Remes et al. |
| 5,365,426 A | 11/1994 | Siegel et al. |
| 5,368,039 A | 11/1994 | Moses |
| 5,370,126 A | 12/1994 | Clifford, Jr. |
| 5,375,610 A | 12/1994 | LaCourse et al. |
| 5,434,419 A | 7/1995 | Decupper |
| 5,435,316 A | 7/1995 | Kruse |

(Continued)

OTHER PUBLICATIONS

U.S. Appl. No. 10/938,783, filed Sep. 10, 2004, Wen.

*Primary Examiner*—Anand Bhatnagar
(74) *Attorney, Agent, or Firm*—Tran & Associates

(57) ABSTRACT

A monitoring system includes one or more cameras to determine a three dimensional (3D) model of a person; means to detect a dangerous condition based on the 3D model; and means to generate a warning when the dangerous condition is detected.

22 Claims, 6 Drawing Sheets

U.S. PATENT DOCUMENTS

| | | |
|---|---|---|
| 5,438,607 A | 8/1995 | Przygoda, Jr. et al. |
| 5,441,047 A | 8/1995 | David et al. |
| 5,458,620 A | 10/1995 | Adams et al. |
| 5,462,065 A | 10/1995 | Cusimano |
| 5,497,781 A | 3/1996 | Chen et al. |
| 5,505,208 A | 4/1996 | Toomim et al. |
| 5,513,651 A | 5/1996 | Cusimano et al. |
| 5,544,649 A * | 8/1996 | David et al. ............ 600/301 |
| 5,544,661 A * | 8/1996 | Davis et al. ............ 600/513 |
| 5,546,953 A | 8/1996 | Garfield |
| 5,551,435 A | 9/1996 | Sramek |
| 5,551,438 A | 9/1996 | Moses |
| 5,579,001 A | 11/1996 | Dempsey et al. |
| 5,579,775 A | 12/1996 | Dempsey et al. |
| 5,584,298 A | 12/1996 | Kabal |
| 5,623,939 A | 4/1997 | Garfield |
| 5,633,910 A * | 5/1997 | Cohen ................. 379/38 |
| 5,652,570 A | 7/1997 | Lepkofker |
| 5,662,118 A | 9/1997 | Skubick |
| 5,671,741 A | 9/1997 | Lang et al. |
| 5,683,425 A | 11/1997 | Hauptmann |
| 5,692,215 A | 11/1997 | Kutzik et al. |
| 5,694,940 A | 12/1997 | Unger et al. |
| 5,708,417 A * | 1/1998 | Tallman et al. ......... 340/539.23 |
| 5,709,215 A | 1/1998 | Perttu et al. |
| 5,710,551 A | 1/1998 | Ridgeway |
| 5,720,771 A | 2/1998 | Snell |
| 5,722,420 A | 3/1998 | Lee |
| 5,733,230 A | 3/1998 | Sawchuck et al. |
| 5,738,104 A | 4/1998 | Lo et al. |
| 5,738,105 A | 4/1998 | Kroll |
| 5,743,268 A | 4/1998 | Kabal |
| 5,772,603 A | 6/1998 | Ohlsson |
| 5,775,330 A | 7/1998 | Kangas et al. |
| 5,776,073 A | 7/1998 | Garfield et al. |
| 5,785,960 A | 7/1998 | Rigg et al. |
| 5,788,643 A | 8/1998 | Feldman |
| 5,857,975 A | 1/1999 | Golub |
| 5,865,755 A | 2/1999 | Golub |
| 5,876,350 A | 3/1999 | Lo et al. |
| 5,935,077 A | 8/1999 | Ogle |
| 5,945,112 A | 8/1999 | Flynn et al. |
| 5,964,719 A | 10/1999 | Costello et al. |
| 5,967,975 A | 10/1999 | Ridgeway |
| 5,987,519 A | 11/1999 | Peifer et al. |
| 5,996,889 A | 12/1999 | Fuchs et al. |
| 6,002,957 A | 12/1999 | Finneran |
| 6,004,312 A | 12/1999 | Finneran et al. |
| 6,010,454 A | 1/2000 | Arieff et al. |
| 6,014,626 A * | 1/2000 | Cohen ................. 704/275 |
| 6,032,035 A | 2/2000 | Webster et al. |
| 6,038,469 A | 3/2000 | Karlsson et al. |
| 6,047,202 A | 4/2000 | Finneran et al. |
| 6,050,940 A | 4/2000 | Braun et al. |
| 6,052,619 A | 4/2000 | John |
| 6,056,671 A | 5/2000 | Marmer |
| 6,063,051 A | 5/2000 | Stern |
| 6,070,140 A | 5/2000 | Tran |
| 6,076,011 A | 6/2000 | Hoover |
| 6,108,685 A | 8/2000 | Kutzik et al. |
| 6,162,151 A * | 12/2000 | Tani et al. ............ 482/54 |
| 6,171,237 B1 | 1/2001 | Avitall |
| 6,175,308 B1 | 1/2001 | Tallman et al. |
| 6,176,831 B1 | 1/2001 | Voss et al. |
| 6,184,797 B1 | 2/2001 | Stark et al. |
| 6,228,034 B1 | 5/2001 | Voss et al. |
| 6,230,056 B1 | 5/2001 | Kroll |
| 6,246,894 B1 | 6/2001 | Steur et al. |
| 6,280,393 B1 | 8/2001 | Granger et al. |
| 6,287,252 B1 | 9/2001 | Lugo |
| 6,299,583 B1 | 10/2001 | Eggers et al. |
| 6,304,797 B1 * | 10/2001 | Shusterman ............ 700/243 |
| 6,336,900 B1 | 1/2002 | Alleckson et al. |
| 6,364,834 B1 | 4/2002 | Reuss et al. |
| 6,364,842 B1 | 4/2002 | Amano et al. |
| 6,368,283 B1 | 4/2002 | Xu et al. |
| 6,374,614 B2 | 4/2002 | Prueitt |
| 6,375,614 B1 | 4/2002 | Braun et al. |
| 6,398,727 B1 | 6/2002 | Bui et al. |
| 6,406,426 B1 | 6/2002 | Reuss et al. |
| 6,413,223 B1 | 7/2002 | Yang et al. |
| 6,416,480 B1 | 7/2002 | Nenov |
| 6,433,690 B2 * | 8/2002 | Petelenz et al. ......... 340/573.1 |
| 6,440,067 B1 | 8/2002 | DeLuca et al. |
| 6,443,906 B1 | 9/2002 | Ting et al. |
| 6,445,299 B1 | 9/2002 | Rojas, Jr. |
| 6,466,816 B2 | 10/2002 | Granger et al. |
| 6,473,640 B1 | 10/2002 | Erlebacher |
| 6,475,146 B1 | 11/2002 | Frelburger et al. |
| 6,475,153 B1 | 11/2002 | Khair et al. |
| 6,487,442 B1 | 11/2002 | Wood |
| 6,514,211 B1 | 2/2003 | Baura |
| 6,515,593 B1 | 2/2003 | Stark et al. |
| 6,533,729 B1 | 3/2003 | Khair et al. |
| 6,544,173 B2 * | 4/2003 | West et al. ............ 600/300 |
| 6,544,174 B2 | 4/2003 | West et al. |
| 6,546,269 B1 | 4/2003 | Kumik |
| 6,554,774 B1 | 4/2003 | Miele |
| 6,556,860 B1 | 4/2003 | Groenewegen |
| 6,595,316 B2 | 7/2003 | Cybulski et al. |
| 6,597,944 B1 | 7/2003 | Hadas |
| 6,605,038 B1 | 8/2003 | Teller et al. |
| 6,609,023 B1 | 8/2003 | Fischer et al. |
| 6,612,984 B1 | 9/2003 | Kerr, II |
| 6,615,074 B2 | 9/2003 | Mickle et al. |
| 6,615,075 B2 | 9/2003 | Mlynash |
| 6,616,613 B1 | 9/2003 | Goodman |
| 6,660,042 B1 | 12/2003 | Curcie et al. |
| 6,661,161 B1 | 12/2003 | Lanzo et al. |
| 6,676,600 B1 | 1/2004 | Conero et al. |
| 6,678,549 B2 | 1/2004 | Cusimano |
| 6,678,551 B2 | 1/2004 | Maalouf et al. |
| 6,687,519 B2 | 2/2004 | Steur et al. |
| 6,705,990 B1 | 3/2004 | Gallant et al. |
| 6,720,984 B1 | 4/2004 | Jorgensen et al. |
| 6,730,038 B2 | 5/2004 | Gallant et al. |
| 6,740,045 B2 | 5/2004 | Amano |
| 6,747,561 B1 | 6/2004 | Reeves |
| 6,760,620 B2 | 7/2004 | Sippens Groenewegen |
| 6,783,492 B2 | 8/2004 | Domiguez et al. |
| 6,804,656 B1 | 10/2004 | Rosenfeld et al. |
| 6,816,266 B2 | 11/2004 | Varshaneya et al. |
| 6,829,501 B2 | 12/2004 | Nielsen et al. |
| 6,832,251 B1 | 12/2004 | Gelvin et al. |
| 6,834,436 B2 | 12/2004 | Townsend et al. |
| 6,843,771 B2 | 1/2005 | Lo et al. |
| 6,856,291 B2 | 2/2005 | Mickle et al. |
| 6,865,409 B2 | 3/2005 | Getsla et al. |
| 6,871,211 B2 | 3/2005 | Labounty et al. |
| 6,882,128 B1 | 4/2005 | Rahmel et al. |
| 6,887,202 B2 | 5/2005 | Currie et al. |
| 6,898,460 B2 | 5/2005 | Hoctor et al. |
| 6,907,288 B2 | 6/2005 | Daum |
| 6,912,420 B2 | 6/2005 | Scheiner et al. |
| 6,944,496 B2 | 9/2005 | Jeong et al. |
| 6,961,285 B2 | 11/2005 | Niemiec et al. |
| 6,965,794 B2 | 11/2005 | Brody |
| 6,973,344 B2 | 12/2005 | Finneran et al. |
| 6,974,419 B1 | 12/2005 | Voss et al. |
| 6,975,206 B2 | 12/2005 | Reining |
| 6,980,852 B2 | 12/2005 | Jersey-Willuhn et al. |
| 6,989,751 B2 | 1/2006 | Richards |
| 7,004,907 B2 | 2/2006 | Banet et al. |
| 7,011,629 B2 | 3/2006 | Bulat |

| | | |
|---|---|---|
| 7,035,679 B2 | 4/2006 | Addison et al. |
| 7,043,293 B1 | 5/2006 | Baura |
| 7,106,885 B2 * | 9/2006 | Osterweil et al. ............ 382/103 |
| 7,110,569 B2 * | 9/2006 | Brodsky et al. ............. 382/103 |
| 2002/0044682 A1 * | 4/2002 | Weil et al. .................... 382/154 |
| 2002/0120184 A1 | 8/2002 | Beck et al. |
| 2003/0004421 A1 | 1/2003 | Ting et al. |
| 2003/0058111 A1 * | 3/2003 | Lee et al. ................. 340/573.1 |
| 2003/0058341 A1 * | 3/2003 | Brodsky et al. ............. 348/169 |
| 2003/0125635 A1 | 7/2003 | Maalouf et al. |
| 2003/0135127 A1 | 7/2003 | Sackner et al. |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |
| 2003/0231115 A1 | 12/2003 | Stanners et al. |
| 2004/0044273 A1 | 3/2004 | Kieth et al. |
| 2004/0102683 A1 | 5/2004 | Khanuja et al. |
| 2004/0122487 A1 | 6/2004 | Hatlestad et al. |
| 2004/0136578 A1 * | 7/2004 | Sieracki et al. ............. 382/128 |
| 2004/0138568 A1 | 7/2004 | Lo et al. |
| 2004/0167409 A1 | 8/2004 | Lo et al. |
| 2004/0167417 A1 | 8/2004 | Schulhauser et al. |
| 2004/0220490 A1 | 11/2004 | Appel et al. |
| 2004/0254493 A1 | 12/2004 | Chervin et al. |
| 2004/0260188 A1 | 12/2004 | Syed et al. |
| 2004/0267148 A1 | 12/2004 | Arand et al. |
| 2005/0038345 A1 | 2/2005 | Gorgenburg et al. |
| 2005/0061568 A1 | 3/2005 | Schondorf et al. |
| 2005/0099387 A1 | 5/2005 | Matsumoto |
| 2005/0113630 A1 | 5/2005 | Fox et al. |
| 2005/0113710 A1 | 5/2005 | Stahmann et al. |
| 2005/0115561 A1 | 6/2005 | Stahmann et al. |
| 2005/0143667 A1 | 6/2005 | Park et al. |
| 2005/0148882 A1 | 7/2005 | Banet |
| 2005/0194926 A1 | 9/2005 | Di Stefano et al. |
| 2005/0201585 A1 | 9/2005 | Jannard et al. |
| 2005/0209521 A1 | 9/2005 | Kettunen et al. |
| 2005/0222515 A1 | 10/2005 | Polyshchuk et al. |
| 2005/0228244 A1 | 10/2005 | Banet et al. |
| 2005/0228299 A1 | 10/2005 | Banet et al. |
| 2005/0228316 A1 | 10/2005 | Morgenstern et al. |
| 2005/0240086 A1 | 10/2005 | Akay et al. |
| 2005/0240523 A1 | 10/2005 | Richardson et al. |
| 2005/0245831 A1 | 11/2005 | Banet et al. |
| 2005/0261594 A1 | 11/2005 | Banet et al. |
| 2005/0261598 A1 | 11/2005 | Banet et al. |
| 2005/0278409 A1 | 12/2005 | Kutzik et al. |
| 2006/0009697 A1 | 1/2006 | Banet et al. |
| 2006/0009698 A1 | 1/2006 | Banet et al. |
| 2006/0047215 A1 | 3/2006 | Newman et al. |
| 2006/0079801 A1 | 4/2006 | DeLuca et al. |
| 2006/0082727 A1 | 4/2006 | Bolger et al. |
| 2006/0084878 A1 | 4/2006 | Banet et al. |
| 2006/0094975 A1 | 5/2006 | Manto |
| 2006/0105357 A1 | 5/2006 | Benesch et al. |

* cited by examiner

| |
|---|
| Place a calibration sheet with known dots at a known distance and perpendicular to a camera view |
| Take snap shot of the sheet, and correlate the position of the dots to the camera image |
| Place a different calibration sheet that contains known dots at another different known distance and perpendicular to camera view. |
| Take snap shot of the sheet and correlate the position of the dots to the camera image |
| Smooth the dots to the pixels to minimize digitization errors |
| For each pixel, draw a line from Dot1(x,y,z) to Dot2 (x, y, z) defining a cone center where the camera can view |

FIG. 2A

Find floor space area

Define camera view background 3D scene

Calculate patient's key features

Detect fall

FIG. 3

Find floor space area

Define camera view background 3D scene

Calculate patient's key features

Extract facial objects

Detect facial orientation

Detect facial expression

FIG. 4

PATIENT MONITORING APPARATUS

BACKGROUND

Improvements in living condition and advances in health care have resulted in a marked prolongation of life expectancy for elderly and disabled population. These individuals, a growing part of society, are dependent upon the delivery of home health and general care, which has its own set of challenges and drawbacks. This population needs continuous general, as well as medical, supervision and care. For example, supervision of daily activities such as dressing, personal hygiene, eating and safety as well as supervision of their health status is necessary. Furthermore, the relief of loneliness and anxiety is a major, yet unsolved, problem that has to be dealt with.

The creation of retirement facilities and old age homes, as well as other geriatric facilities, provides only a partial solution to the problems facing the geriatric population. As discussed in U.S. Pat. Nos. 5,544,649 and 6,433,690, the notion of ambulatory (home environment) patient care is gaining increased popularity and importance. As discussed in the '649 patent, the number of old aged people receiving home care services under Medicare has shown a 13% annual growth rate and has tripled in 10 years (1978-1988) from 769,000 to 2.59 million. This shift in patient care from the "sheltered" institutional milieu to the patient's home, work place, or recreational environment is driven in part by cost and in part to a new care concept that prefers keeping the aged and the disabled in their own natural environment for as long as possible.

Typically, home care is carried out either by the patient's family or by nonprofessional help. The monitoring equipment at home care facilities is usually minimal or nonexistent, and the patient has to be transported to the doctor's office or other diagnostic facility to allow proper evaluation and treatment. Patient follow-up is done by means of home visits of nurses which are of sporadic nature, time consuming and generally very expensive. A visiting nurse can perform about 5-6 home visits per day. The visits have to be short and can usually not be carried out on a daily basis. Moreover, a visiting nurse program provides no facilities for continuous monitoring of the patient and thus no care, except in fortuitous circumstances, in times of emergency. The remainder of day after the visiting nurse has left is often a period of isolation and loneliness for the elderly patient.

In outpatient care, health-threatening falls are an important epidemiological problem in this growing segment of the population. Studies indicate that approximately two thirds of accidents in people 65 years of age or older, and a large percentage of deaths from injuries, are due to falls. Approximately 1.6 million hip fracture injuries worldwide in 1990 were due to falls, and that this number will increase 6.26% by 2050, with the highest incidences recorded in Northern Europe and North America. In the elderly, 90% of hip fractures happen at age 70 and older, and 90% are due to falls. The falls are usually due (80%) to pathological balance and gait disorders and not to overwhelming external force (i.e., being pushed over by some force). More than 50% of elderly persons suffer from arthritis and/or orthopedic impairments, which frequently leads to falls. Specifically prone to falls are women experiencing a higher percentage of arthritis-related structural bone changes. It is estimated that approximately 5% of falls result in fracture and 1% of all falls are hip fractures. The percentages vary slightly in different geographical regions (e.g., Japan, Scandinavia), but the consensus of the available research is that the falls are a significant epidemiological problem in the growing elderly population.

The physiological and medical results of a fall range from grazes, cuts, sprains, bruising, fractures, broken bones, torn ligaments, permanent injuries and death. The most common fall-related injuries are lacerations and fractures, the most common area of fracture being the hip and wrist. Damage to areas such as the hip and legs can result in permanent damage and increased likelihood or further falls and injuries.

Falls in the elderly can produce social and mental as well as physiological repercussions. Anguish and reduced confidence in mobility can complicate problems and even increase the probability of falls and severity of fall-related injuries from lack of exercise and tensing of muscles.

Among older people in the U.S. (age 65+) there are approximately 750,000 falls per year requiring hospitalization due to either bone fracturing (approx. 480,000 cases) or hip fracturing (approx. 270,000 cases). The result of such injuries is an average hospital stay between 2 and 8 days. Assuming the average cost of $1,000 per hospital day, a total cost of falls in the elderly for the health care industry can be estimated at three billion dollars per year. This figure is likely to increase as the older age segment of the population increases.

BRIEF DESCRIPTION OF THE DRAWINGS

FIG. 2A illustrates a process for determining three dimensional (3D) detection.

FIG. 3 illustrates a process for detecting falls.

FIG. 4 illustrates a process for detecting facial expressions.

SUMMARY

Figure 1:
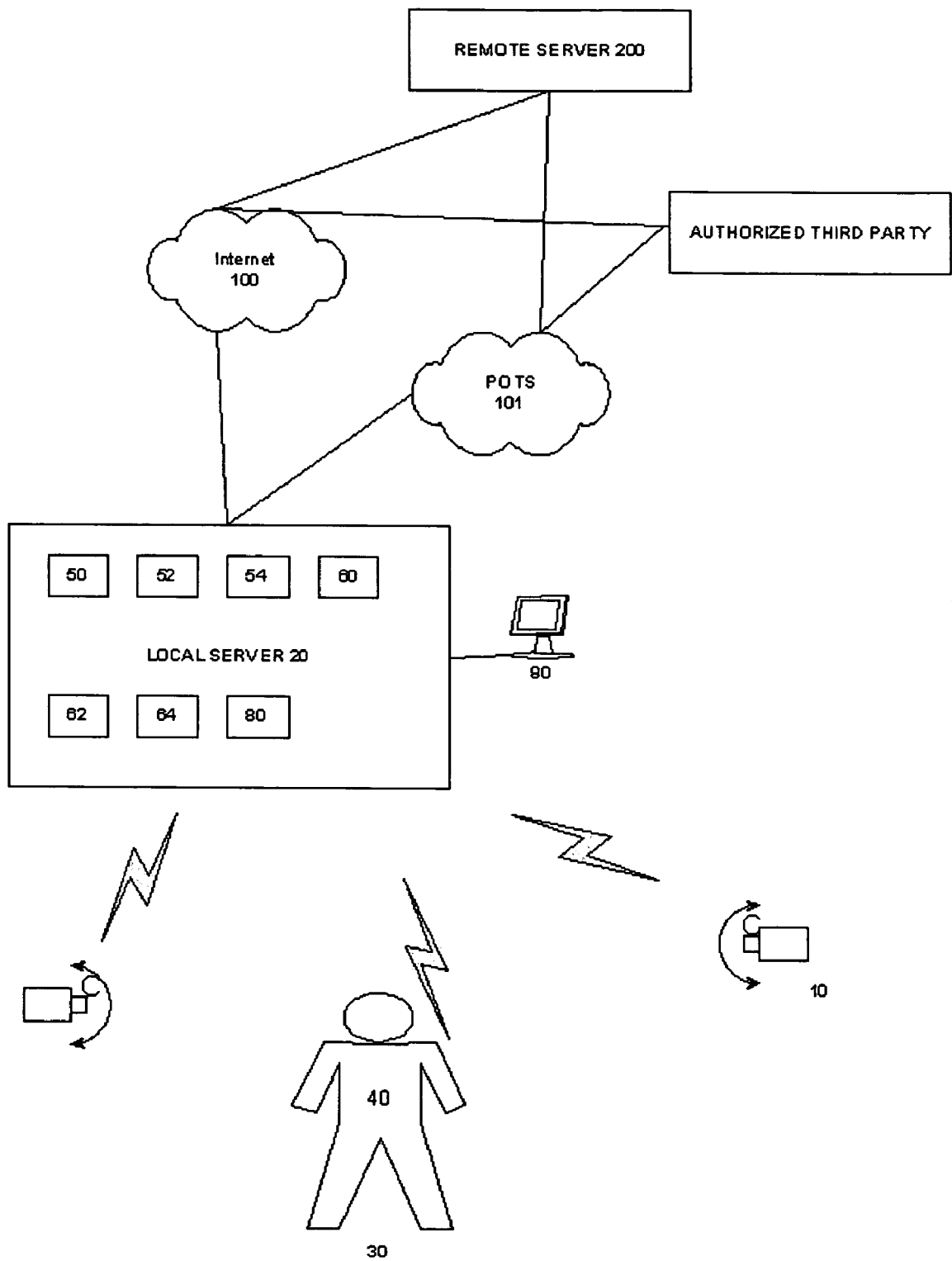
FIG. 1 illustrates an exemplary embodiment for monitoring a person.

A monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

Advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The patient's home equipment is simple to use and modular to allow for the accommodation of the monitoring device to the specific needs of each patient. Moreover, the system is simple to install.

DESCRIPTION

FIG. 1 shows an exemplary home monitoring system. In this system, a plurality of monitoring cameras 10 are placed in various predetermined positions in a home of a patient 30. The cameras 10 can be wired or wireless. For example, the cameras can communicate over infrared links or over radio links conforming to the 802.11X (e.g. 802.11A, 802.11B, 802.11G) standard or the Bluetooth standard to a server 20. The server 20 stores images and videos of patient's ambulation pattern.

The patient 30 may wear one or more sensors 40, for example devices for sensing ECG, EKG, blood pressure, sugar level, among others. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wristband and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module 52 monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0,0,0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line. In one embodiment shown in FIG. 2A, each camera is calibrated before 3D detection is done. Pseudo-code for one implementation of a camera calibration process is as follows:

Place a calibration sheet with known dots at a known distance (e.g. 1 meter), and perpendicular to a camera view.

Take snap shot of the sheet, and correlate the position of the dots to the camera image:

Dot1(x,y, 1)←→pixel (x,y)

Place a different calibration sheet that contains known dots at another different known distance (e.g. 2 meters), and perpendicular to camera view.

Take another snapshot of the sheet, and correlate the position of the dots to the camera image:

$$Dot2(x,y, 2) \leftarrow\!\!\!\rightarrow pixel\ (x,y)$$

Smooth the dots and pixels to minimize digitization errors. By smoothing the map using a global map function, step errors will be eliminated and each pixel will be mapped to a cone space.

For each pixel, draw a line from Dot1 (x,y,z) to Dot2 (x, y, z) defining a cone center where the camera can view.

One smoothing method is to apply a weighted filter for Dot1 and Dot2. A weight filter can be used. In one example, the following exemplary filter is applied.

| | | |
|---|---|---|
| 1 | 2 | 1 |
| 2 | 4 | 2 |
| 1 | 2 | 1 |

Assuming Dot1_Left refers to the value of the dot on the left side of Dot1 and Dot1_Right refers to the value of the dot to the right of Dot1 and Dot1_Upper refers to the dot above Dot1, for example, the resulting smoothed Dot1 value is as follows:

$$\tfrac{1}{16}*(Dot1*4+Dot1\_Left*2+Dot1\_Right*2+$$
$$Dot1\_Upper*2+Dot1\_Down*2+$$
$$Dot1\_UpperLeft+Dot1\_UpperRight+$$
$$Dot1\_LowerLeft+Dot1\_LowerRight)$$

Similarly, the resulting smoothed Dot2 value is as follows:

$$\tfrac{1}{16}*(Dot2*4+Dot2\_Left*2+Dot2\_Right*2+$$
$$Dot2\_Upper*2+Dot2\_Down*2+$$
$$Dot2\_UpperLeft+Dot2\_UpperRight+$$
$$Dot2\_LowerLeft+Dot2\_LowerRight)$$

In another smoothing method, features from Dot1 sheet are mapped to a sub pixel level and features of Dot2 sheet are mapped to a sub pixel level and smooth them. To illustrate, Dot1 dot center (5, 5, 1) are mapped to pixel (1.05, 2.86), and Dot2 dot center (10, 10, 2) are mapped to pixel (1.15, 2.76). A predetermined correlation function is then applied.

Figure 2B:
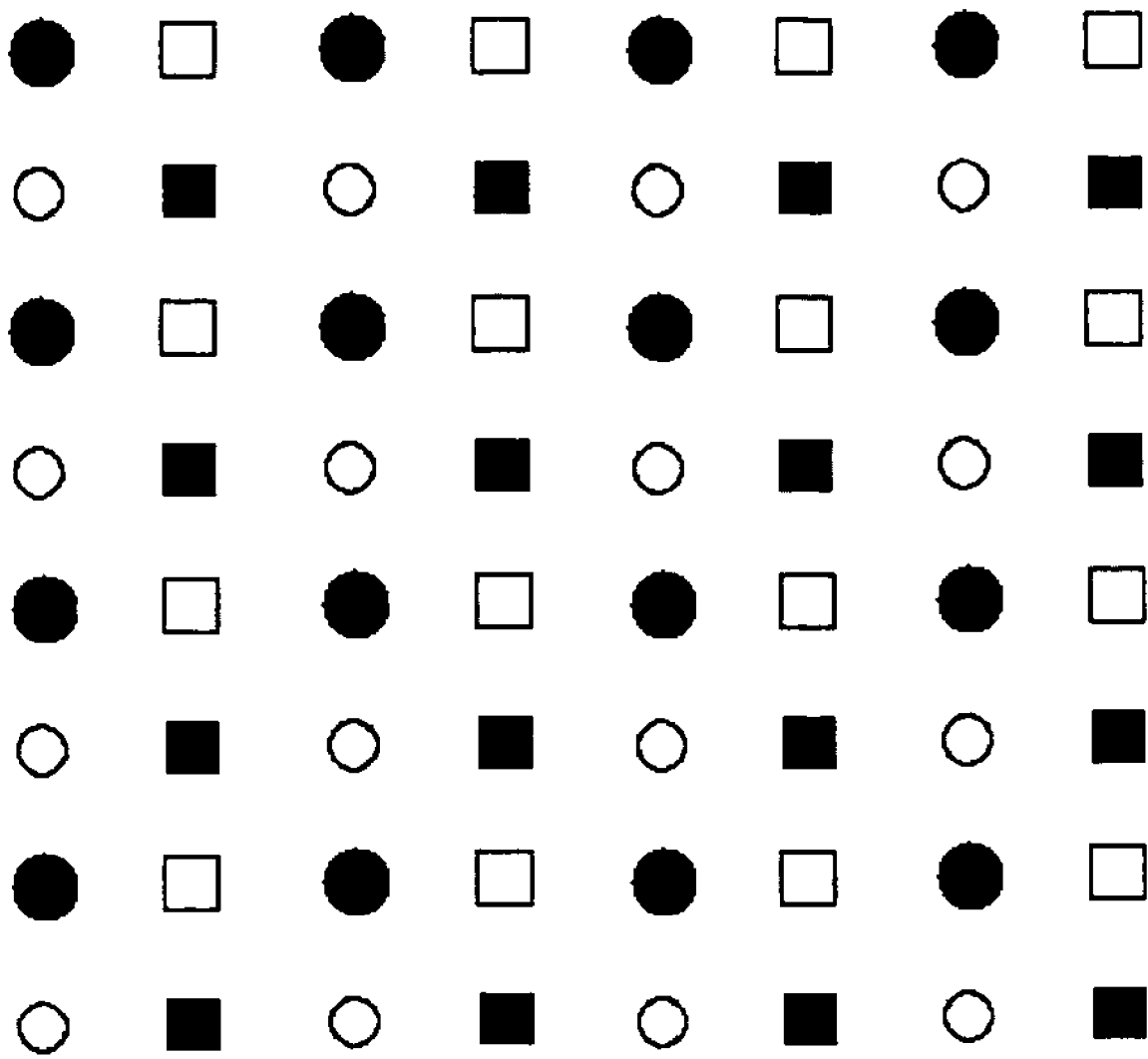
FIG. 2B shows an exemplary calibration sheet.

FIG. 2B shows an exemplary calibration sheet having a plurality of dots. In this embodiment, the dots can be circular dots and square dots which are interleaved among each others. The dots should be placed relatively close to each other and each dot size should not be too large, so we can have as many dots as possible in one snapshot. However, the dots should not be placed too close to each other and the dot size should not be too small, so they are not identifiable.

A module 54 monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that patient had taken a bath or a shower. However, if a person falls and remains motionless for a predetermined period, the system would record the event and notify a designated person to get assistance.

A fall detection process (shown in FIG. 3) performs the following operations:

Find floor space area
Define camera view background 3D scene
Calculate patient's key features
Detect fall In one implementation, pseudo-code for determining the floor space area is as follows:

1. Sample the camera view space by M by N, e.g. M=1000, N=500.
2. Calculate all sample points the 3D coordinates in room coordinate system; where Z axis is pointing up. Refer to the 3D detection for how to calculate 3D positions.
3. Find the lowest Z value point (Zmin)
4. Find all points whose Z values are less than Zmin+Ztol; where Ztol is a user adjustable value, e.g. 2 inches.
5. If rooms have different elevation levels, then excluding the lowest Z floor points, repeat step 2, 3 and 4 while keeping the lowest Z is within Ztol2 of previous Z. In this example Ztol2=2 feet, which means the floor level difference should be within 2 feet.
6. Detect stairs by finding approximate same flat area but within equal Z differences between them.
7. Optionally, additional information from the user can be used to define floor space more accurately, especially in single camera system where the coordinates are less accurate, e.g.:
   a. Import the CAD file from constructors' blue prints.
   b. Pick regions from the camera space to define the floor, then use software to calculate its room coordinates.
   c. User software to find all flat surfaces, e.g. floors, counter tops, then user pick the ones, which are actually floors and/or stairs.

In the implementation, pseudo-code for determining the camera view background 3D scene is as follows:

1. With the same sample points, calculate x, y coordinates and the Z depth and calculate 3D positions.
2. Determine background scene using one the following methods, among others:
   a. When there is nobody in the room.
   b. Retrieve and update the previous calculated background scene.
   c. Continuous updating every sample point when the furthest Z value was found, that is the background value.

In the implementation, pseudo-code for determining key features of the patient is as follows:

1. Foreground objects can be extracted by comparing each sample point's Z value to the background scene point's Z value, if it is smaller, then it is on the foreground.
2. In normal condition, the feet/shoe can be detected by finding the lowest Z point clouds close the floor in room space, its color will be extracted.
3. In normal condition, the hair/hat can be detected by finding the highest Z point clouds close the floor in room space, its color will be extracted.

4. The rest of the features can be determined by searching from either head or toe. E.g, hat, hair, face, eye, mouth, ear, earring, neck, lipstick, moustache, jacket, limbs, belt, ring, hand, etc.
5. The key dimension of features will be determined by retrieving the historic stored data or recalculated, e.g., head size, mouth width, arm length, leg length, waist, etc.
6. In abnormal conditions, features can be detected by detect individual features then correlated them to different body parts. E.g, if patient's skin is black, we can hardly get a yellow or white face, by detecting eye and nose, we know which part is the face, then we can detect other characteristics.

To detect fall, the pseudo-code for the embodiment is as follows:
1. The fall has to be detected in almost real time by tracking movements of key features very quickly. E.g. if patient has black hair/face, track the center of the black blob will know roughly where his head move to.
2. Then the center of mass will be tracked, center of mass is usually around belly button area, so the belt or borderline between upper and lower body closed will be good indications.
3. Patient's fall always coupled with rapid deceleration of center of mass. Software can adjust this threshold based on patient age, height and physical conditions.
4. Then if the fall is accidental and patient has difficult to get up, one or more of following will happen:
   a. Patient will move very slowly to find support object to get up.
   b. Patient will wave hand to camera ask for help. To detect this condition, the patient hand has to be detected first by finding a blob of points with his skin color. Hand motion can be tracked by calculate the motion of the center of the points, if it swings left and right, it means patient is waving to camera.
   c. Patient is unconscious, motionless. To detect this condition, extract the foreground object, calculate its motion vectors, if it is within certain tolerance, it means patient is not moving. In the mean time, test how long it last, if it past a user defined time threshold, it means patient is in great danger.

In one embodiment for fall detection, the system determines a patient fall-down as when the patient's knee, butt or hand is on the floor. The fall action is defined a quick deceleration of center of mass, which is around belly button area. An accidental fall action is defined when the patient falls down with limited movement for a predetermined period.

The system monitors the patients' fall relative to a floor. In one embodiment, the plan of the floor is specified in advance by the patient. Alternatively, the system can automatically determine the floor layout by examining the movement of the patient's feet and estimated the surfaces touched by the feet as the floor.

The system detects a patient fall by detecting a center of mass of an exemplary feature. Thus, the software can monitor the center of one or more objects, for example the head and toe, the patient's belt, the bottom line of the shirt, or the top line of the pants.

The detection of the fall can be adjusted based on two thresholds:
a. Speed of deceleration of the center of mass.
b. The amount of time that the patient lies motionless on the floor after the fall.

In one example, once a stroke occurs, the system detects a slow motion of patient as the patient rests or a quick motion as the patient collapses. By adjust the sensitivity threshold, the system detects whether a patient is uncomfortable and ready to rest or collapse.

If the center of mass movement ceases to move for a predetermined period, the system can generate the warning. In another embodiment, before generating the warning, the system can request the patient to confirm that he or she does not need assistance. The confirmation can be in the form of a button that the user can press to override the warning. Alternatively, the confirmation can be in the form of a single utterance that is then detected by a speech recognizer.

In another embodiment, the confirmatory signal is a patient gesture. The patient can nod his or her head to request help and can shake the head to cancel the help request. Alternatively, the patient can use a plurality of hand gestures to signal to the server 20 the actions that the patient desires.

By adding other detecting mechanism such as sweat detection, the system can know whether patient is uncomfortable or not. Other items that can be monitored include chest movement (frequency and amplitude) and rest length when the patient sits still in one area, among others.

Besides monitoring for falls, the system performs video analysis of the patient. For example, during a particular day, the system can determine the amount of time for exercise, sleep, entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the camera 10 view for a predetermined period and does not show up anywhere else in the house, the system infers that patient had taken a bath or a shower. However, if a person falls and remains motionless for a predetermined period, the system would record the event and notify a designated person to get assistance.

In one embodiment, changes in the patient's skin color can be detected by measuring the current light environment, properly calibrating color space between two photos, and then determining global color change between two states. Thus, when the patient's face turn red, based on the redness, a severity level warning is generated.

In another embodiment, changes in the patient's face are detected by analyzing a texture distortion in the images. If the patient perspires heavily, the texture will show small glisters, make-up smudges, or sweat/tear drippings. Another example is, when long stretched face will be detected as texture distortion. Agony will show certain wrinkle texture patterns, among others.

The system can also utilize high light changes. Thus, when the patient sweats or changes facial appearance, different high light areas are shown, glisters reflect light and pop up geometry generates more high light areas.

A module 62 analyzes facial changes such as facial asymmetries. The change will be detected by superimpose a newly acquired 3D anatomy structure to a historical (normal) 3D anatomy structure to detect face/eye sagging or excess stretch of facial muscles.

In one embodiment, the system determines a set of base 3D shapes, which are a set of shapes which can represent extremes of certain facial effects, e.g. frown, open mouth, smiling, among others. The rest of the 3D face shape can be generated by blending/interpolating these base shapes by applied different weight to each base shapes.

The base 3D shape can be captured using 1) a 3D camera such as cameras from Steinbichler, Genex Technology, Minolta 3D, Olympus 3D or 2) one or more 2D camera with preset camera field of view (FOV) parameters. To make it more accurate, one or more special markers can be placed on patient's face. For example, a known dimension square stick can be placed on the forehead for camera calibration purposes.

Using the above 3D detection method, facial shapes are then extracted. The proper features (e.g. a wrinkle) will be detected and attached to each base shape. These features can be animated or blended by changing the weight of different shape(s). The proper features change can be detected and determine what type of facial shape it will be.

Next, the system super-imposes two 3D facial shapes (historical or normal facial shapes and current facial shapes). By matching features and geometry of changing areas on the face, closely blended shapes can be matched and facial shape change detection can be performed. By overlaying the two shapes, the abnormal facial change such as sagging eyes or mouth can be detected.

The above processes are used to determine paralysis of specific regions of the face or disorders in the peripheral or central nervous system (trigeminal paralysis; CVA, among others). The software also detects eyelid positions for evidence of ptosis (incomplete opening of one or both eyelids) as a sign of innervation problems (CVA; Homer syndrome, for example). The software also checks eye movements for pathological conditions, mainly of neurological origin are reflected in aberrations in eye movement. Pupil reaction is also checked for abnormal reaction of the pupil to light (pupil gets smaller the stronger the light) may indicate various pathological conditions mainly of the nervous system. In patients treated for glaucoma pupillary status and motion pattern may be important to the follow-up of adequate treatment. The software also checks for asymmetry in tongue movement, which is usually indicative of neurological problems. Another check is neck veins: Engorgement of the neck veins may be an indication of heart failure or obstruction of normal blood flow from the head and upper extremities to the heart. The software also analyzes the face, which is usually a mirror of the emotional state of the observed subject. Fear, joy, anger, apathy are only some of the emotions that can be readily detected, facial expressions of emotions are relatively uniform regardless of age, sex, race, etc. This relative uniformity allows for the creation of computer programs attempting to automatically diagnose people's emotional states.

Speech recognition is performed to determine a change in the form of speech (slurred speech, difficulties in the formation of words, for example) may indicated neurological problems, such an observation can also indicate some outward effects of various drugs or toxic agents.

In one embodiment shown in FIG. 4, a facial expression analysis process performs the following operations:

Find floor space area

Define camera view background 3D scene

Calculate patient's key features

Extract facial objects

Detect facial orientation

Detect facial expression

The first three steps are already discussed above. The patient's key features provide information on the location of the face, and once the face area has been determined, other features can be detected by detecting relative position to each other and special characteristics of the features:

Eye: pupil can be detected by applying Chamfer matching algorithm, by using stock pupil objects.

Hair: located on the top of the head, using previous stored hair color to locate the hair point clouds.

Birthmarks, wrinkles and tattoos: pre store all these features then use Chamfer matching to locate them.

Nose: nose bridge and nose holes usually show special characteristics for detection, sometime depend on the view angle, is side view, special silhouette will be shown.

Eye browse, Lips and Moustache: All these features have special colors, e.g. red lipstick; and base shape, e.g. patient has no expression with mouth closed. Software will locate these features by color matching, then try to deform the base shape based on expression, and match shape with expression, we can detect objects and expression at the same time.

Teeth, earring, necklace: All these features can be detected by color and style, which will give extra information.

In one implementation, pseudo-code for detecting facial orientation is as follows:

Detect forehead area

Use the previously determined features and superimpose them on the base face model to detect a patient face orientation.

Depends on where patient is facing, for a side facing view, silhouette edges will provide unique view information because there is a one to one correspondent between the view and silhouette shape.

Once the patient's face has been aligned to the right view, exemplary pseudo code to detect facial expression is as follows:

1. Detect shape change. The shape can be match by superimpose different expression shapes to current shape, and judge by minimum discrepancy. E.g. wide mouth open.
2. Detect occlusion. Sometime the expression can be detected by occlusal of another objects, e.g., teeth show up means mouth is open.
3. Detect texture map change. The expression can relate to certain texture changes, if patient smile, certain wrinkles patents will show up.
4. Detect highlight change. The expression can relate to certain high light changes, if patient sweats or cries, different highlight area will show up.

A module 80 communicates with a third party such as the police department, a security monitoring center, or a call center. The module 80 operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

During operation, the module 80 checks whether broadband network is available. If broadband network is available, the module 80 allows high resolution video, among others, to be broadcasted directly from the server 20 to the third party or indirectly from the server 20 to the remote server 200 to the third party. In parallel, the module 80 allows sound to be transmitted using the telephone circuit. In this manner, high resolution video can be transmitted since sound data is separately sent through the POTS network.

If broadband network is not available, the system relies on the POTS telephone network for transmission of voice and images. In this system, one or more images are compressed for burst transmission, and at the request of the third party or the remote server 200, the telephone's sound system is placed on hold for a brief period to allow transmission of images over the POTS network. In this manner, existing POTS lifeline telephone can be used to monitor patients. The resolution and quantity of images are selectable by the third party. Thus, using only the lifeline as a communication medium, the person monitoring the patient can elect to only listen, to view one high resolution image with duplex telephone voice transmission, to view a few low resolution images, to view a compressed stream of low resolution video with digitized voice, among others.

During installation or while no live person in the scene, each camera will capture its own environment objects and store it as background images, the software then detect the live person in the scene, changes of the live person, so only the portion of live person will be send to the local server, other compression techniques will be applied, e.g. send changing file, balanced video streaming based on change.

The local server will control and schedule how the video/picture will be send, e.g. when the camera is view an empty room, no pictures will be sent, the local server will also determine which camera is at the right view, and request only the corresponding video be sent. The local server will determine which feature it is interested in looking at, e.g. face and request only that portion be sent.

With predetermined background images and local server controlled streaming, the system will enable higher resolution and more camera system by using narrower bandwidth.

Through this module, a police officer, a security agent, or a healthcare agent such as a physician at a remote location can engage, in interactive visual communication with the patient. The patient's health data or audio-visual signal can be remotely accessed. The patient also has access to a video transmission of the third party. Should the patient experience health symptoms requiring intervention and immediate care, the health care practitioner at the central station may summon help from an emergency services provider. The emergency services provider may send an ambulance, fire department personnel, family member, or other emergency personnel to the patient's remote location. The emergency services provider may, perhaps, be an ambulance facility, a police station, the local fire department, or any suitable support facility.

Communication between the patient's remote location and the central station can be initiated by a variety of techniques. One method is by manually or automatically placing a call on the telephone to the patient's home or from the patient's home to the central station.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives images from the server 20 and passes the data to one or more remote servers 200. The images are transmitted from the server 20 over a secure communication link such as virtual private network (VPN) to the remote server(s) 200.

The server 20 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 20 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

Next, the transactions between the server 20 and one of the remote servers 200 are detailed. The server 20 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64 k or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 20 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

In one implementation, the servers 200 use RAID-5 striping and parity techniques to organize data in a fault tolerant and efficient manner. The RAID (Redundant Array of Inexpensive Disks) approach is well described in the literature and has various levels of operation, including RAID-5, and the data organization can achieve data storage in a fault tolerant and load balanced manner. RAID-5 provides that the stored data is spread among three or more disk drives, in a redundant manner, so that even if one of the disk drives fails, the data stored on the drive can be recovered in an efficient and error free manner from the other storage locations. This method also advantageously makes use of each of the disk drives in relatively equal and substantially parallel operations. Accordingly, if one has a six gigabyte cluster volume which spans three disk drives, each disk drive would be responsible for servicing two gigabytes of the cluster volume. Each two gigabyte drive would be comprised of one-third redundant information, to provide the redundant, and thus fault tolerant, operation required for the RAID-5 approach. For additional physical security, the server can be stored in a Fire Safe or other secured box, so there is no chance to erase the recorded data, this is very important for forensic analysis.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. The RF tag is an integrated circuit that is coupled with a mini-antenna to transmit data. The circuit contains memory that stores the identification Code and other pertinent data to be transmitted when the chip is activated or interrogated using radio energy from a reader. A reader consists of an RF antenna, transceiver and a microprocessor. The transceiver sends activation signals to and receives identification data from the tag. The antenna may be enclosed with the reader or located outside the reader as a separate piece. RFID readers communicate directly with the RFID tags and send encrypted usage data over the patient's network to the server 20 and eventually over the Internet 100. The readers can be built directly into the walls or the cabinet doors.

In one embodiment, capacitively coupled RFID tags are used. The capacitive RFID tag includes a silicon microprocessor that can store 96 bits of information, including the pharmaceutical manufacturer, drug name, usage instruction and a 40-bit serial number. A conductive carbon ink acts as the tag's antenna and is applied to a paper substrate through conventional printing means. The silicon chip is attached to printed carbon-ink electrodes on the back of a paper label, creating a low-cost, disposable tag that can be integrated on the drug label. The information stored on the drug labels is written in a Medicine Markup Language (MML), which is based on the extensible Markup Language (XML). MML would allow all computers to communicate with any computer system in a similar way that Web servers read Hyper Text Markup Language (HTML), the common language used to create Web pages.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 20 can order these items automatically. The server 20 also monitors drug compliance, and if the patient does not remove the bottle to dispense medication as prescribed, the server 20 sends a warning to the healthcare provider.

Figure 5:
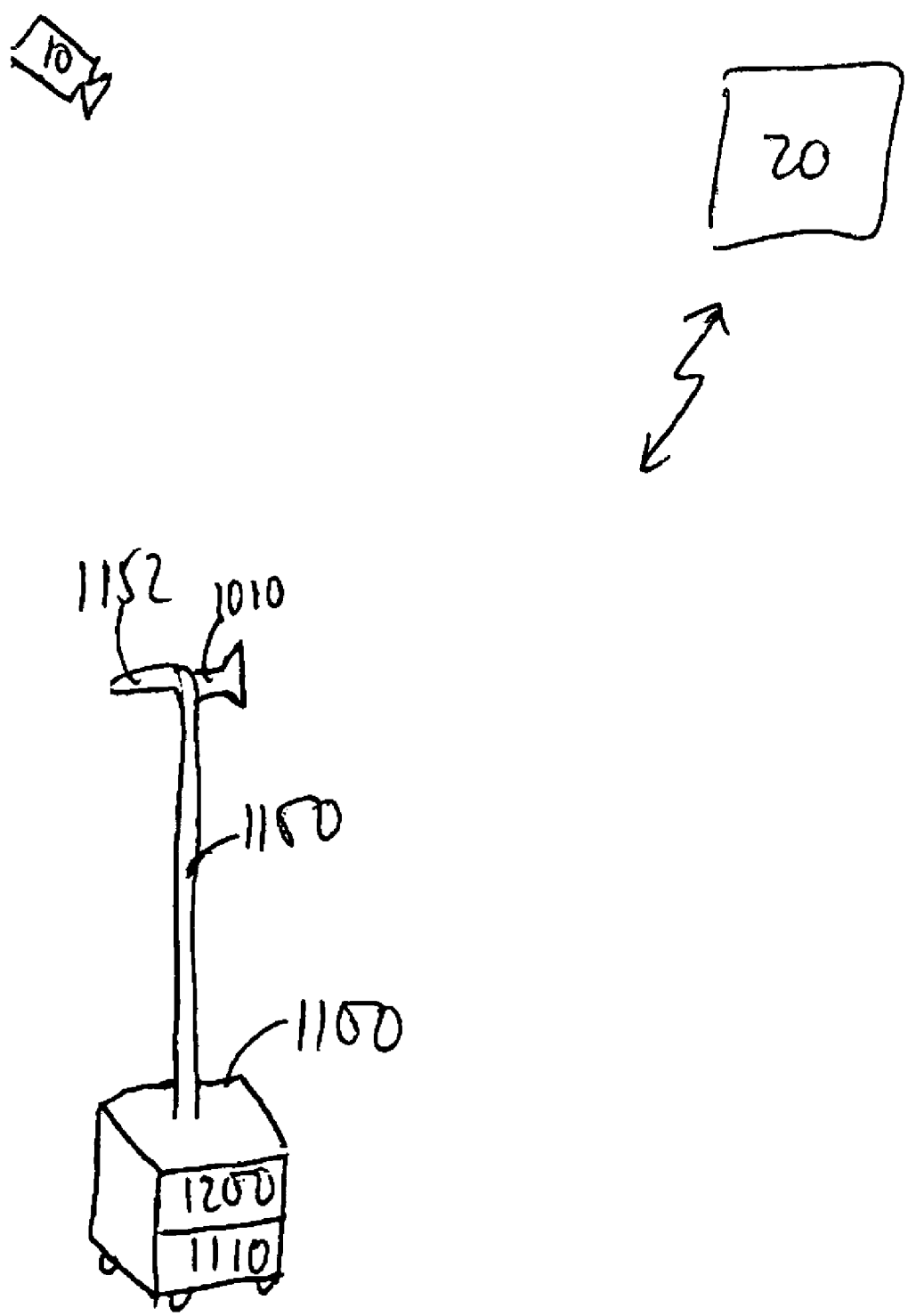
FIG. 5 illustrates a smart cane that works with the embodiment of FIG. 1.

Due to its awareness of the patient's position, the server 20 can optionally control a mobility assistance device such as a smart cane. FIG. 5 shows an exemplary robot 1000 for assisting the patient in ambulating his or her home. The robot embodiment of FIG. 5 is essentially a smart cane with a camera 1010, a frame 1100 with drive systems 1110 having stepper motors, wheels, belts and pulleys, mounted to a mounting plate. The robot 1000 also has control module 1200 including a processor, memory, camera, display, wireless networking, and data storage devices. In one embodiment, the control module 1200 is a PC compatible laptop computer.

The robot 1000 sends video from its camera to the server 20, which in turn coordinates the position of the robot 1000, as determined by the cameras 10 mounted in the home as well as the robot camera. The robot position, as determined by the server 20, is then transmitted to the robot 1000 for navigation.

In this smart cane embodiment, the frame 1100 has an extended handle 1150. The handle 1150 includes handle sensors 1152 mounted thereon to detect the force places on each handle to receive as input the movement desired by the patient. In one embodiment, the robot 1000 has a control navigation system that accepts patient command as well as robot self-guidance command. The mobility is a result of give-and-take between the patient's self-propulsion and the walker's automated reactions. Thus, when the patient moves the handle to the right, the robot determines that the patient is interested in turning and actuates the drive systems 1110 appropriately. However, if the patient is turning into an obstacle, as determined by the cameras and the server 20, the drive system provides gentle resistance that tells the patient of an impending collision.

If, for example, a patient does not see a coffee table ahead, the walker will detect it, override the patient's steering to avoid it, and thereby prevent a possible fall. Onboard software processes the data from 180 degrees of approaching terrain and steers the front wheel toward openings and away from obstacles.

The control module 1200 executes software that enables the robot 1000 to move around its environment safely. The software performs localization, mapping, path planning and obstacle avoidance. In one embodiment, images from a plurality of wall-mounted cameras 10 are transmitted to the server 20. The server 20 collects images of the robot and triangulates the robot position by cross-referencing the images. The information is then correlated with the image from the robot-mounted camera 1010 and optical encoders 1011 that count the wheel rotations to calculate traveled distance for range measurement. In this process, a visual map of unique "landmarks" created as the robot moves along its path is annotated with the robot's position to indicate the position estimate of the landmark. The current image, seen from the robot, is compared with the images in the database to find matching landmarks. Such matches are used to update the position of the robot according to the relative position of the matching landmark. By repeatedly updating the position of landmarks based on new data, the software incrementally improves the map by calculating more accurate estimates for the position of the landmarks. An improved map results in more accurate robot position estimates. Better position estimates contribute to better estimates for the landmark positions and so on. If the environment changes so much that the robot no longer recognizes previous landmarks, the robot automatically updates the map with new landmarks. Outdated landmarks that are no longer recognized can easily be deleted from the map by simply determining if they were seen or matched when expected.

Using the obstacle avoidance algorithm, the robot generates corrective movements to avoid obstacles not represented in the path planner such as open/closed doors, furniture, people, and more. The robot rapidly detects obstacles using its sensors and controls its speed and heading to avoid obstacles.

The hazard avoidance mechanisms provide a reflexive response to hazardous situations to insure the robot's safety and guarantee that it does not damage itself or the environment. Mechanisms for hazard avoidance include collision detection using not one but a complementary set of sensors and techniques. For instance, collision avoidance can be provided using contact sensing, motor load sensing, and vision. The combination of multiple sources for collision detection guarantees safe collision avoidance. Collision detection provides a last resort for negotiating obstacles in case obstacle avoidance fails to do so in the first place, which can be caused by moving objects or software and hardware failures.

If the walker is in motion (as determined by the wheel encoder), the force applied to the brake pads is inversely proportional to the distance to obstacles. If the walker is stopped, the brakes should be fully applied to provide a stable base on which the patient can rest. When the walker is stopped and the patient wishes to move again, the brakes should come off slowly to prevent the walker from lurching forward The walker should mostly follow the patient's commands, as this is crucial for patient acceptance. For the safety braking and the safety braking and steering control systems, the control system only influences the motion when obstacles or cliffs are near the patient. In other words, the walker is, typically, fully patient controlled. For all other situations, the control system submits to the patient's desire. This does not mean that the control system shuts down, or does not provide the usual safety features. In fact, all of the control systems fall back on their emergency braking to keep the patient safe. When the control system has had to brake to avoid an obstacle or has given up trying to lead the patient on a particular path, the patient must disengage the brakes (via a pushbutton) or re-engage the path following (again via a pushbutton) to regain control or allow collaboration again. This lets the patient select the walker's mode manually when they disagree with the control system's choices.

While the foregoing addresses the needs of the elderly, the system can assist infants as well. Much attention has been given to ways to reduce a risk of dying from Sudden Infant Death Syndrome (SIDS), an affliction which threatens infants who have died in their sleep for heretofore unknown reasons. Many different explanations for this syndrome and ways to prevent the syndrome are found in the literature. It is thought that infants which sleep on their backs may be at risk of death because of the danger of formula regurgitation and liquid aspiration into the lungs. It has been thought that infants of six (6) months or less do not have the motor skills or body muscular development to regulate movements responsive to correcting breathing problems that may occur during sleep.

In an exemplary system to detect and minimize SIDS problem in an infant patient, a diaper pad is used to hold an array of integrated sensors and the pad can be placed over a diaper, clothing, or blanket. The integrated sensors can provide data for measuring position, temperature, sound, vibration, movement, and optionally other physical properties through additional sensors. Each pad can have sensors that provide one or more of the above data. The sensors can be added or removed as necessary depending on the type of data being collected.

The sensor should be water proof and disposable. The sensor can be switch on /off locally or remotely. The sensor can be removalable or clip on easily. The sensor can store or beam out information for analysis purpose, e.g. store body temperature every 5 seconds. The sensor can be turn-on for other purposed, e.g. diaper wet, it will beep and allow a baby care provider to take care of the business in time. The array of sensors can be self selective, e.g., when one sensor can detect strong heart beat, it will turn off others to do so.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution: approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery. In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing ECG, EKG, blood pressure, sugar level, among others. In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In one embodiment, the sensors for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A monitoring system, comprising:
   one or more cameras to determine a three dimensional (3D) body model of a person;
   a processor coupled to the one or more cameras to process the 3D body model to detect a dangerous condition based on the 3D model with computer readable code to detect the person's fall including:
     computer readable code to detect a falling speed of the person's center-of-mass (threshold 1);
     computer readable code to detect when a body part touches a floor; and
     computer readable code to detect a time span without center-of-mass motion after fall (threshold 2); and
   a device to generate a warning when the dangerous condition is detected.

2. The system of claim 1, wherein one of the cameras is a 3D camera.

3. The system of claim 1, wherein one of the cameras is a 2D camera, further comprising wherein the processor to converts 2D images to the 3D model.

4. The system of claim 1, wherein the processor detects confirmatory signals from the person.

5. The system of claim 4, wherein the confirmatory signal includes a head movement, a hand movement, or a mouth movement.

6. The system of claim 4, wherein the confirmatory signal includes the person's voice.

7. The system of claim 1, further comprising a network to communicate images of the 3D model to a remote computer.

8. The system of claim 7, wherein the data to be sent to a local server is reduced by controlling which camera and what portion of images to be sent based on motion information.

9. The system of claim 7, wherein the images are encrypted or scrambled for privacy.

10. The system of claim 7, further comprising a network to allow the person and a remote viewer to visually communicate with each other.

11. The system of claim 7, wherein the viewer includes a doctor, a nurse, a medical assistant, or a caregiver.

12. The system of claim 11, wherein the fall detector comprises a global positioning system (GPS) receiver to detect movement and where the person falls.

13. The system of claim 1, wherein the body part includes a knee, a butt, or a hand.

14. The system of claim 1, further comprising computer readable code to adjust threshold 1 and threshold 2.

15. The system of claim 1, further comprising computer readable code to store and analyze patient information.

16. The system of claim 15, wherein the patient information includes medicine taking habits, eating and drinking habits, sleeping habits, or excise habits.

17. The system of claim 1, further comprising a patient interface for accessing information.

18. The system of claim 1, further comprising computer readable code to secure data relating to the person.

19. The system of claim 1, further comprising one or more local server(s) adapted to receive images of the person.

20. The system of claim 19, wherein the local server stores and analyzes information relating to the person's ambulation.

21. A monitoring system, comprising:
   one or more cameras to determine a three diminsinonal (3D) body model of a person;
   a processor coupled to the one or more cameras to process the 3D body model to detect a dangerous condition based on the 3D model;
   a device to generate a warning when the dangerous condition is detected; and
   a patient interface including:
     a touch screen;
     voice-activated text reading; and
     one touch telephone dialing.

22. A monitoring system, comprising:
   one or more cameras positioned to capture three dimensional (3D) body model of the patient; and
   a server coupled to the one or more cameras, the server executing code to process the 3D model, to detect a dangerous condition for the patient based on a center of mass of the 3D body model and to allow a remote third party to view images of the patient when the dangerous condition is detected, the code including:
   computer readable code to detect a falling speed of the person's center-of-mass (threshold 1);
   computer readable code to detect when a body part touches a floor; and
   computer readable code to detect a time span without center-of-mass motion after fall (threshold 2).

* * * * *